US010689260B2

(12) United States Patent
Mochalin et al.

(10) Patent No.: US 10,689,260 B2
(45) Date of Patent: Jun. 23, 2020

(54) SALT-ASSISTED ULTRASONIC DISAGGREGATION OF NANODIAMOND

(71) Applicant: The Curators of the University of Missouri, Columbia, MO (US)

(72) Inventors: Vadym Mochalin, Rolla, MO (US); Kostiantyn Turcheniuk, Rolla, MO (US); Caleb Trecazzi, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 392 days.

(21) Appl. No.: 15/799,051

(22) Filed: Oct. 31, 2017

(65) Prior Publication Data

US 2018/0134563 A1    May 17, 2018

Related U.S. Application Data

(60) Provisional application No. 62/420,646, filed on Nov. 11, 2016.

(51) Int. Cl.

| | | |
|---|---|---|
| *C01B 32/28* | (2017.01) | |
| *B02C 23/06* | (2006.01) | |
| *B02C 23/08* | (2006.01) | |
| *B02C 19/18* | (2006.01) | |
| *B02C 23/18* | (2006.01) | |
| *B01J 19/10* | (2006.01) | |
| *A61K 47/02* | (2006.01) | |

(52) U.S. Cl.
CPC ............. *C01B 32/28* (2017.08); *A61K 47/02* (2013.01); *B01J 19/10* (2013.01); *B02C 19/18* (2013.01); *B02C 23/06* (2013.01); *B02C 23/08* (2013.01); *B02C 23/18* (2013.01); *C01P 2004/64* (2013.01)

(58) Field of Classification Search
CPC .......... C01B 32/28; B01J 19/10; B02C 23/18; B02C 19/18; B02C 23/08; B02C 23/06; A61K 47/02; C01P 2004/64
USPC ....................................... 204/157.42, 157.47
See application file for complete search history.

(56) References Cited

U.S. PATENT DOCUMENTS

| | | | |
|---|---|---|---|
| 7,690,589 B2 * | 4/2010 | Kerns ................... | B01F 3/1221 241/101.8 |
| 8,703,665 B2 | 4/2014 | Branson et al. | |
| 2005/0008560 A1* | 1/2005 | Kataoka ................ | B82Y 40/00 423/445 R |

(Continued)

FOREIGN PATENT DOCUMENTS

| | | |
|---|---|---|
| WO | 2010121323 A1 | 10/2010 |
| WO | 2012158380 A1 | 11/2012 |

OTHER PUBLICATIONS

"Salt-Assisted Ultrasonic Deaggregation of Nanodiamond," Turcheniuk et al, ACS Appl. Mater. Interfaces 2016, 8, 25461-25468 (Year: 2016).*

(Continued)

*Primary Examiner* — Nicholas A Smith
*Assistant Examiner* — Colleen M Raphael
(74) *Attorney, Agent, or Firm* — Stinson LLP

(57) ABSTRACT

Methods for disaggregating nanodiamond clusters, for example, by using ultrasound to break apart nanodiamond aggregates in a sodium chloride aqueous slurry. Compositions, such as aqueous nanodiamond dispersions and dry particulate compositions that may be produced using these methods.

21 Claims, 10 Drawing Sheets

(56) References Cited

U.S. PATENT DOCUMENTS

| | | | |
|---|---|---|---|
| 2009/0224435 A1* | 9/2009 | Gogotsi | B01J 23/52 264/442 |
| 2014/0314850 A1* | 10/2014 | Badea | C07C 59/68 424/489 |
| 2015/0038593 A1 | 2/2015 | Gogotsi et al. | |
| 2016/0221831 A1* | 8/2016 | Bakr | C01B 32/28 |
| 2017/0240429 A1* | 8/2017 | Yamakawa | B82Y 40/00 |

OTHER PUBLICATIONS

Derwent abstract of RU2357017C1 (Year: 2009).*

Eidelman, E.D., et al., "A Stable Suspenskion of Single Ultrananocrystalline Diamond Particles," Sep. 26, 2005, Diamond & Related Materials, 14:1765-1769, 5 pages.

Krueger, A., et al., "Deagglomeration and Functionalisation of Detonation Diamond," Sep. 4, 2007, Phys Stat Sol (a), 204/9:2881-2887, 7 pages.

Mchedlov-Petrossyan, N.O., et al., Colloidal Properties and Behaviors of 3 nm Primary Particles of Detonation Nanodiamonds in Aqueous Media, Jun. 28, 2015, Phys Chem Chem Phys, 17:16186-16203, 18 pages.

Turcheniuk, K., et al., "Salt-Assisted Ultrasonic Deaggregation of Nanodiamond," Sep. 2, 2016, ACS Appl Mater Interfaces, 8 pages.

* cited by examiner

US 10,689,260 B2

SALT-ASSISTED ULTRASONIC DISAGGREGATION OF NANODIAMOND

REFERENCE TO RELATED APPLICATION

This application claims priority to U.S. application No. 62/420,646 filed Nov. 11, 2016, the entire disclosure of which is incorporated by reference.

FIELD OF THE INVENTION

This application describes methods for disaggregating nanodiamond clusters, as well as compositions produced using these methods.

BACKGROUND

Nanodiamonds have numerous useful properties, ranging from lubrication, to nanofillers for polymer and metal composites, and to medical applications. Nanodiamonds produced through a detonation process are biocompatible, inexpensive to produce, and scalable. Recently, progress in preparing aqueous dispersions of nanodiamonds has facilitated their use both in biomedical field and in polymer composites.

Many existing and potential applications in the biomedical and pharmaceutical fields, in particular, depend upon nanodiamonds having a very small average particle size. For example, nanoparticles having a particle size within the range of 10-100 nanometers can be suspended and circulate within blood, and are readily removed from the bloodstream by the kidneys. Nanoparticles smaller than 10 nanometers have several additional properties, such as the ability to penetrate the blood-brain barrier or a cell's nuclear pore complex, that are highly desirable in biomedical applications.

Unfortunately, nanodiamonds have a strong tendency to aggregate, forming strongly-bound aggregates comprising 10, 20, or even 100 or more primary nanodiamond particles. Detonation nanodiamond particles, in particular, are known to form aggregates that cannot be destroyed by traditional means such as sonication or milling. It is therefore highly desirable to develop methods of disaggregating nanodiamond clusters and obtaining single-digit nanodiamonds (i.e., single digit nanodiamonds having a diameter of smaller than 10 nanometers).

Several disaggregation methods for nanodiamond suspensions are known in the art, including ball milling, attrition milling, and bead-assisted sonic disintegration (BASD). Each of these techniques can be used to obtain single-digit nanodiamond suspensions. Unfortunately, each of the known disaggregation techniques possesses one or more significant disadvantages. For example, many known disaggregation techniques introduce impurities into the nanodiamond material, which presents a significant concern in the biomedical context. In addition, many known disaggregation methods are complex, require expensive custom-made equipment, and/or significantly increase the cost of obtaining single-digit nanodiamonds.

Recently, U.S. Patent Application Publication No. 2015/0038593, which is herein incorporated by reference, disclosed a dry media-assisted attrition milling process that utilized crystalline milling media, such as sodium chloride or sucrose, to disaggregate nanodiamond clusters. This process provided several significant improvements relative to previously known wet milling processes, which had required the use of zirconia as the milling media.

Unfortunately, the process disclosed in the '593 publication still presents a number of drawbacks that limit its usefulness in preparing disaggregated nanodiamonds for biomedical applications. In addition to being relatively expensive and costly to maintain, attrition mills use steel jars, shafts and balls, which represent sources of metal contaminants and are subjected to severe wear and corrosion during the milling process, especially in the presence of salt. As a result, nanodiamonds produced using the process described in the '593 publication are often contaminated with metal impurities, including iron and other components of the steel. While many of the metal impurities are soluble in acids, they require the use of an additional purification step that reduces the overall efficiency and adds to the cost and complexity of the process. Additionally, while the process described in the '593 publication can reduce the size of the nanodiamond aggregates down to an average diameter of 30-50 nanometers, single-digit nanodiamonds cannot be obtained unless the dispersion pH is adjusted to approximately 11 upon completion of the milling. This requires the introduction of yet another process step, and adds still more cost and complexity.

It is therefore highly desirable to develop a method for disaggregating nanodiamonds that is inexpensive, easy to implement, and does not introduce unwanted impurities into the nanodiamond material.

SUMMARY

Briefly, therefore, provided herein is a method of disaggregating nanodiamond clusters combining aggregated nanodiamond clusters with a disaggregating agent in a liquid, which is a solvent for the disaggregating agent, with the disaggregating agent being present in a concentration above its solubility limit in the solvent to form a mixture of solvent, solid disaggregating agent, dissolved disaggregating agent, and nanodiamond clusters; and sonicating the slurry for a time sufficient to produce nanodiamond particles having a median particle size less than the median particle size of the aggregated nanodiamond clusters, wherein a mass ratio of disaggregating agent to nanodiamond particles in the liquid medium is from about 10:1 to about 100:1, or from about 25:1 to about 75:1, such as about 35:1 to about 50:1.

Other objects and features will be in part apparent and in part pointed out hereinafter.

DETAILED DESCRIPTION

Figure 1A:
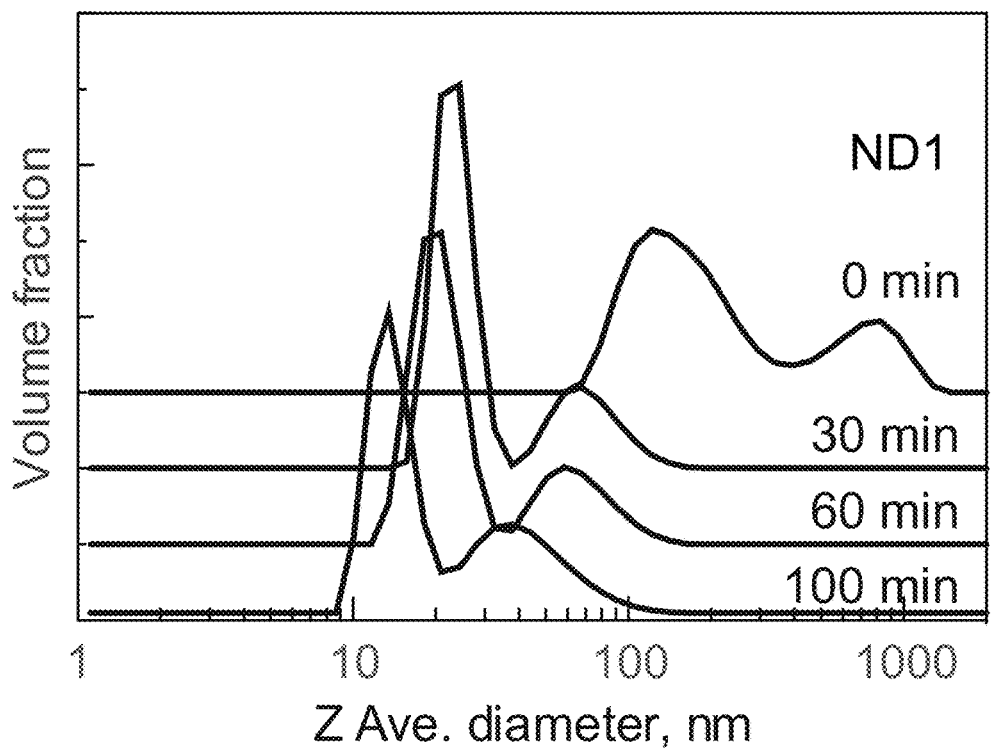
FIGS. 1A and 1B depict the particle size distribution of nanodiamond aqueous dispersions discussed in Example 1.

Provided herein are methods of disaggregating nanodiamond clusters by salt-assisted ultrasonic disaggregation (SAUD). The methods described herein are useful, for example, to produce compositions comprising nanodiamonds having an average particle size of less than 10 nanometers in diameter.

The methods described herein may provide a number of advantages relative to previously known methods of disaggregating nanodiamonds. For example, no pH adjustment of the nanodiamond dispersion is required. More significantly, the method does not introduce any irremovable or difficult-to-remove contaminants into the resulting nanodiamonds—an important advantage in applications for which high purity nanodiamonds are necessary, particularly biomedical applications. The processes described herein generally do not require costly materials or expensive equipment, such as zirconia microbeads or attrition mills, and can be implemented by virtually any laboratory or scaled up for large-scale production, for instance, by employing continuous flow sonication cells. Additionally, nanodiamonds produced using the processes described herein can be dried and then redispersed to form a colloidal dispersion of nanodiamonds that retain a relatively small particle size, which represents another advantage compared to previously known disaggregation techniques.

As used herein, the terms "nanodiamond aggregates," "aggregated nanodiamonds," and "aggregated nanodiamond clusters" each refer to those nanodiamond aggregates comprising a multiplicity of primary nanodiamond particles, for example nanodiamond aggregates comprising at least 10, 20, 30, 40, 50, 100, or 1000 or more primary nanodiamond particles.

As used herein, the term "disaggregating" refers to the breaking apart of said aggregate clusters into smaller clusters (i.e., containing fewer primary particles) down to and including individual primary nanodiamond particles.

As used herein, the term "particle size" is defined as the diameter of the smallest circular hole through which a particle (which includes an aggregation of particles) can pass freely. For example, the particle size of a spherical aggregate is equivalent to the diameter of the aggregate, while the particle size of an ellipsoidal aggregate corresponds to the length of the longest minor axis.

In the methods described herein, aggregated nanodiamond clusters may be combined with a disaggregating agent in a liquid medium. The resulting composition may then be sonicated for a time sufficient to produce nanodiamond particles having a median particle size less than the median particle size of the initial aggregated nanodiamond clusters. This process may be referred to herein as salt-assisted ultrasonic disaggregation.

As described in greater detail below, the liquid medium is in the form of a dispersion, suspension, or slurry, wherein the dispersed or discontinuous solid phase comprises the disaggregating agent and the nanodiamonds.

Once the composition has been sonicated for a time sufficient to reduce the median particle size of the nanodiamonds to within the desired range, at least a portion of the disaggregating agent may be separated from the nanodiamonds. This separation may be accomplished, for example, by dissolving the disaggregating agent in an eluting solvent in which the nanodiamonds are relatively insoluble, but in which the disaggregating agent is soluble. This eluting solvent may be the same as or different from the primary solvent in which the disaggregation is performed. The nanodiamonds may then be separated from the solution comprising the disaggregating agent. Non-limiting examples of suitable separation techniques include centrifugation, electrostatic separation, hydrodynamic separation, froth flotation, and magnetic separation, among others.

The solubility of the disaggregating agent in an eluting solvent facilitates full separation of the disaggregating agent—by dissolution—from the disaggregated nanodiamond primary particles after the disaggregating process. This contrasts with prior art processes that use insoluble milling media, such as zirconia or metal spheres. Accordingly, in preferred embodiments, the disaggregating process is performed in the absence of insoluble milling media, such as ceramic or metallic milling media, which are insoluble in the selected primary solvent and/or eluting solvent. It is particularly preferred that the process is performed in the absense of milling media comprising zirconium.

To further reduce the presence of the disaggregating agent as an impurity in the resulting nanodiamond product, the separation step may be repeated multiple times to achieve the desired level of purity. Preferably, at least about 50% of the disaggregating agent is removed, more preferably at least about 75%, at least about 90%, at least about 95%, or even at least about 99%. Most preferably, substantially all of the disaggregating agent is removed from the nanodiamond product.

As described above, sonication may be carried out for a time sufficient to reduce the median particle size of the nanodiamonds to within a desired range. Suitable frequency, intensity, and duration of the sonication will depend upon the desired nanodiamond particle size and the particular equipment used. Such optimization is well within the skill of the ordinary artisan.

For example, the period of sonication may range from about 5 minutes to about 300 minutes. The sonication may be carried out for at least about 5 minutes, about 10 minutes, about 15 minutes, about 20 minutes, about 30 minutes, or about 60 minutes. Exemplary ranges include from about 5 minutes to about 180 minutes, about 5 minutes to about 120 minutes, and about 30 minutes to about 120 minutes.

The sonication frequency may range from about 20 kHz to about 100 kHz. For example, the sonication frequency may be at least about 30 kHz, about 40 kHz, or about 50 kHz. Exemplary ranges include from about 20 kHz to about 80 kHz, about 20 kHz to about 60 kHz, and about 50 kHz to about 100 kHz.

The power delivered by the sonicator may range, for example, from about 50 watts to about 1500 watts. The sonication power may be at least about 100 watts, at least about 250 watts, about 500 watts, or about 1000 watts. Exemplary ranges include from about 500 watts to about 1500 watts, about 50 watts to about 1000 watts, and about 250 watts to about 1500 watts.

Nanodiamond Surface Functionalization

In the processes described herein, it is desirable to use nanodiamonds that are purified and that are generally free of contaminants. It is further desirable to utilize nanodiamonds that comprise hydrophilic surface groups, and in particular nanodiamonds that comprise surface carboxyl groups.

In some embodiments, the nanodiamonds comprise at least about 0.5 mmol of carboxyl groups per gram of nanodiamond, for example at least about 0.1 mmol of carboxyl groups per gram of nanodiamond, at least about 0.5 mmol of carboxyl groups per gram of nanodiamond, at least about 1 mmol of carboxyl groups per gram of nanodiamond, or at least about 2 mmol of carboxyl groups per gram of nanodiamond. For example, the nanodiamonds may comprise from about 0.1 mmol to about 10 mmol of carboxyl groups per gram of nanodiamond, from about 0.5 mmol to about 5 mmol of carboxyl groups per gram of nanodiamond, or from about 1 mmol to about 3 mmol of carboxyl groups per gram of nanodiamond.

Without being bound to a particular theory, it is believed that the processes described herein are more efficient when applied to hydrophilic nanodiamonds that have a large number of carboxyl groups on the surface. Fortunately, virtually any nanodiamond can be made amenable to salt-assisted ultrasonic disaggregation after a simple air oxidation step, which removes non-diamond carbon and forms carboxyl (COOH) groups on the surface. Other techniques to introduce surface carboxyl groups to nanodiamonds are generally known to those skilled in the art and include liquid oxidation, microwave-assisted liquid oxidation, and gas phase (e.g., ozone) oxidation techniques.

Accordingly, the methods described herein may comprise an air oxidation step wherein the nanodiamond aggregates are purified prior to the disaggregation step. Air oxidation can be carried out as a matter of routine by those having skill in the art, and typically involves heating the nanodiamond sample (e.g., at a temperature of at least about 350° C., at least about 375° C., or at least about 420° C.) in air for a sufficient period (e.g., a period of at least about 5 minutes, at least about 15 minutes, at least about 30 minutes, at least about 45 minutes, at least about 1 hour, or at least about 2 hours).

In some embodiments, the nanodiamonds comprise surface carboxyl groups and the disaggregating agent comprises a salt. It is believed that when the disaggregating agent comprises a salt that dissociates in the liquid medium, the cation may react with the surface carboxyl groups to form the corresponding salt. As an example, when the disaggregating agent comprises sodium chloride, sodium carboxylate groups may be formed on the surface of the nanodiamonds.

Without being bound to a particular theory, it is believed that the electrostatic repulsion provided by anionic surface groups (e.g., carboxyl groups) may assist with the disaggregation process and prevent re-aggregation of the nanodiamond particles. Surface carboxylate groups (e.g., sodium carboxylate) may dissociate to a greater extent than surface carboxyl groups, and may therefore provide a further enhancement of the disaggregation process.

Disaggregating Agent

In the processes described herein, the disaggregating agent comes into contact with the nanodiamond aggregates, breaking them apart and reducing their effective particle size. Typically, the disaggregating agent is a crystalline material.

The disaggregating agent may comprise a crystalline inorganic salt. For example, the disaggregating agent may comprise an alkali metal, alkaline earth metal, or ammonium salt of bicarbonate, bisulfate, carbonate, halide, hydrogen carbonate, hydrogen sulfate, metabisulfite, nitrate, sulfite, hydroxide, sulfate, or thiosulfate. The disaggregating agent may comprise one or more amine or ammonium salts, including but not limited to ammonium bromide, ammonium carbonate, ammonium chloride, and methylamine hydrochloride. The disaggregating agent may comprise one or more crystalline hydroxides, hydrogen carbonates, or hydrogen carbonates of pharmaceutically acceptable alkali metals, including but not limited to sodium, potassium, lithium, calcium, and barium; sodium hydrogen sulfate, sodium hydrogen carbonate, sodium hydroxide; sodium sulfate, sodium chloride, sodium metabisulfite, sodium thiosulfate, Glauber's salt, sodium bisulfate, magnesium sulfate, potassium chloride, sodium carbonate, sodium bicarbonate, potassium carbonate, potassium bicarbonate, potassium bromide, and potash alum.

The disaggregating agent preferably comprises a halide salt, such as the halide salt of an alkali metal or alkaline earth metal, and more preferably a chloride salt such as sodium chloride. The sodium chloride may be provided in dendritic, granular, or ordinary cubic form.

Alternatively, the disaggregating agent may comprise a crystalline sugar, organic acid, or organic acid salt. Non-limiting examples of suitable crystalline sugars include those comprising lactose, maltose, sucrose, and mixtures thereof. Non-limiting examples of suitable organic acids and salts include formic acid, acetic acid, propionic acid, byturic acid, valeric acid, caproic acid, lactic acid, succinic acid, fumaric acid, maleic acid, tartaric acid, citric acid, benzoic acid and derivatives thereof, para-toluenesulphonic acid, phenol, uric acid, trifluoromethane sulphonic acid, phosphonic acid, aminomethylphosphonic acid, and pharmaceutically acceptable salts and mixtures thereof. For example, the disaggregating agent may comprise sucrose.

As a further alternative, the disaggregating agent may comprise an organic crystalline compound other than a sugar. For example, the disaggregating agent may comprise one or more phenols or quinones.

In applications where the nanodiamonds are used to form metal-matrix composites, whether for improving mechanical properties of metal or for biomedical applications, such as magnetic imaging or anticancer therapy, or for other applications, the disaggregating agent may comprise a metal salt. For example, the disaggregating agent may comprise a chloride, sulfate, or nitrate of gadolinium, copper, nickel, iron, or cobalt. Non-limiting examples of suitable disaggregating agents include cuprous chloride, cupric chloride, cupric sulfate, cupric nitrate, cuprous acetate, cupric acetate, nickel chloride, nickel sulfate, nickel nitrate, nickel acetate, ferrous chloride, ferric chloride, ferrous sulfate, ferric sulfate, ferric nitrate, ferric acetate, ferrous acetate, cobalt(II) chloride, cobalt(II) sulfate, cobalt(II) acetate, and cobalt(II) nitrate.

Preferably, the particle or crystal size of the disaggregating agent is similar to the median particle size of the aggregated nanodiamond clusters. For example, the initial crystal or particle size of the disaggregating agent crystal may be on the order of 0.1-10 microns, which may be similar, in certain embodiments, to the initial median particle size of the aggregated nanodiamond clusters. The disaggregating agent and the aggregated nanodiamond may then be reduced in size at a comparable rate, and thus maintain relatively similar particle sizes throughout the sonication process.

As described above, it is preferred that the disaggregating agent be soluble in an eluting solvent in which the nanodiamonds are relatively insoluble; this property facilitates complete or nearly complete removal of the disaggregating agent from the nanodiamond product using centrifugation and/or washing that can be carried out by one skilled in the art.

When the nanodiamonds are for use in biomedical or pharmaceutical appplications, it is desirable that the disaggregating agent be generally recognized as safe (GRAS) by the pharmaceutical industry, such that any portion of disaggregating agent that remains as an impurity in the nanodiamond product would not be considered harmful.

Solvent

The disaggregating process in one aspect involves combining aggregated nanodiamond clusters with a disaggregating agent in a liquid medium comprising a solvent, with the disaggregating agent being present in a concentration above its solubility limit in the solvent. In a preferred embodiment, this mixture consists essentially of the three components of the clusters, disaggregating agent, and solvent, with there being no other components which materially affect the mechanism by which the clusters are disaggregated. In another preferred embodiment, the mixtures consist only of these three components. The methods described herein may utilize a solvent in which the disaggregating agent is at least partially soluble, and in which the nanodiamonds are relatively insoluble. Water is a preferred solvent.

Alternatively, the methods may utilize a non-aqueous organic solvent. Non-limiting examples of suitable solvents include tetrahydrofuran, chloroform, 2-methyl tetrahydrofuran, ethyl acetate, dichloromethane, dichloroethane, butyl acetate, dimethylformamide, dimethyl sulfoxide, ethanol, methanol, ethylene glycol, propylene glycol, diglyme, hexane, heptane, octane, and other higher hydrocarbons, diethylcarbonate, benzene, and toluene, ionic liquids, acetonitrile, propylene carbonate, among others.

In addition to the primary solvent that is a component of the sonicated mixture in combination with the clusters and disaggregating agent to be sonicated, there is in many embodiments an eluting solvent as mentioned above used for separating the disaggregating agent from the disaggregated clusters after the disaggregation/sonication operation. In a preferred embodiment, this eluting solvent is water. In other embodiments, this eluting solvent may be, for example, glycerin, dimethylformamide, and propylene glycol.

Component Ratios

In order to provide a sufficiently dense environment for the methods described herein to be carried out efficiently, the disaggregating agent should be present in significant excess relative to the nanodiamond. For example, the mass ratio of the disaggregating agent to the nanodiamond may be at least about 5:1, at least about 10:1, at least about 20:1, at least about 30:1, at least about 40:1, at least about 50:1, at least about 75:1, at least about 100:1, at least about 125:1, at least about 150:1, or at least about 200:1. In preferred embodiments, the mass ratio of the disaggregating agent to the nanodiamond is from 10:1 to about 300:1, such as from about 10:1 to about 100:1, or from about 25:1 to about 75:1, such as about 35:1 to about 50:1. One currently preferred ratio is about 40:1. If the ratio is too low (i.e., the relative proportion of disaggregating agent is too small), the process does not achieve efficient and complete disaggregation of the clusters into primary nanodiamond particles. If the ratio is too high, the medium is too thick and the transfer of ultrasound energy to the clusters is inefficient and compromised.

The concentration of the nanodiamond in the liquid medium should also be sufficiently high to enable efficient disaggregation. For example, the nanodiamond may be present in an amount of at least 10 grams per liter of the liquid medium, such as at least about 20 g/L, at least about 30 g/L, at least about 40 g/L, or at least about 50 g/L.

In some embodiments, the disaggregating agent is insoluble in the solvent component. In other embodiments, the disaggregating agent is at least partially soluble in the solvent component, and the liquid medium comprises the disaggregating agent in an amount that exceeds its solubility limit in the solvent component. For example, the liquid medium may be supersaturated such that the disaggregating agent is present in an amount of greater than 100%, such as greater than 125%, greater than 150%, greater than 175%, or greater than 200% of its solubility limit.

A ratio of solvent to disaggregating agent is also important, as it is important that it be low enough that a substantial portion of the disaggregating agent is in slurry or dispersion rather than dissolved, so that a substantial undissolved portion of the disaggregating agent is available for physical collision with the clusters to be disaggregated. For example, the ratio of the mass of the solvent to the mass of the disaggregating agent is typically less than about 4:1, such as less than about 3:1, less than about 2:1, or less than about 1.5:1. Exemplary ranges for this ratio are between about 0.25:1 and 4:1, and between about 0.5:1 and about 1.5:1. For example, in embodiments where the solvent comprises water and the disaggregating agent comprises sodium chloride, the mass ratio of water to sodium chloride may be from about 0.25:1 to about 2:1, more preferably from about 0.5:1 to about 1.5:1, and most preferably about 1:1.

The invention in one aspect involves an overall three-way weight ratio solvent to disaggregating agent to nanodiamond clusters that is carefully controlled. In one embodiment, for example, the weight ratio of solvent:disaggregating agent:clusters is between about 20:40:1 and in another embodiment it is about 40:40:1. As a general proposition, in certain embodiments this ratio is controlled to be in the range between 25:100:1 and 40:10:1, such as between 40:75:1 and 40:25:1. These three-way weight ratios are particularly preferred in embodiments where the solvent is water and the disaggregating agent is sodium chloride.

Particle Size Reduction

The methods described herein may be used to produce nanodiamond particles having a median particle size of of less than about 50 nm, less than about 40 nm, less than about 30 nm, less than about 25 nm, less than about 20 nm, or less than about 15 nm. The nanodiamond particles have a median effective particle size of at least about 2 nm; and preferably less than 10 nm, for example less than about 9 nm, less than about 8 nm, less than about 7 nm, less than about 6 nm, or even less than about 5 nm.

As used herein, the terms "median effective particle size" and "median particle size" mean that 50% of the nanodiamond particles have a particle size of less than the stated value. The methods described herein may be used to produce nanodiamond particles wherein greater than 50% of said particles have a particle size of less than one of the values listed above. For example, at least about 60%, at least about 70%, at least about 80%, at least about 90%, at least about 95%, at least about 98%, or at least about 99% of the nanodiamond particles may have a particle size of less than one of the values listed above.

The dynamic viscosity of nanodiamond colloid may be measured by conventional methods known to those skilled in art. For example, the dynamic viscosity of a disaggregated nanodiamond slurry, prepared using the methods described herein, may range from at least about 0.8 mPa·s to 5 mPa·s at a temperature of about 25° C.

As a non-limiting example, in one series of embodiments, the methods described herein may be used to produce nanodiamond particles wherein at least about 60%, at least about 70%, at least about 80%, at least about 90%, at least about 95%, at least about 98%, or at least about 99% of said nanodiamond particles have a particle size of less than about 20 nm, such as between 2 nm and about 20 nm. In a second series of embodiments, the methods described herein may be used to produce nanodiamond particles wherein at least about 60%, at least about 70%, at least about 80%, at least about 90%, at least about 95%, at least about 98%, or at least about 99% of said nanodiamond particles have a particle size of less than about 10 nm, such as between 2 nm and about 10 nm.

The size of nanodiamond particles in a given sample may be measured by conventional particle size measuring techniques known to those skilled in the art. Non-limiting examples of suitable particle size measuring techniques include sedimentation field flow fractionation, photon correlation spectroscopy, disk centrifugation, and static and dynamic light scattering.

Nanodiamond Particles and Compositions

In other aspects, the present invention is directed to nanodiamond particles prepared using the methods described herein. Still further aspects are directed to compositions comprising said nanodiamond particles. Non-limiting examples of compositions within the scope of the invention include dry powders, aqueous dispersions, and colloidal dispersions comprising said nanodiamond particles.

For example, pharmaceutical compositions comprising nanodiamond particles prepared using the methods described herein are within the scope of the present invention.

The nanodiamonds may be characterized by a median particle size within the ranges described above. Likewise, the compositions may be characterized in that they comprise nanodiamonds having a median particle size within the ranges described above.

Aqueous dispersions of nanodiamonds prepared according to the methods described herein may be substantially free of aggregates having a particle size greater than about 250 nm, greater than about 200, greater than about 100 nm, greater than about 90 nm, greater than about 70 nm, greater than about 60 nm, or greater than about 50 nm. As used herein, the term "substantially free of aggregates" means that the dispersion comprises less than 10 vol %, for example less than 5 vol %, less than 2 vol %, or even less than 1 vol % of said aggregates, relative to the total solid volume of the nanodiamonds present in the dispersion.

Nanodiamond particles prepared according to the methods described herein may be further characterized by an isoelectric point (IEP) of less than about 7, less than about 6, less than about 5, less than about 4, or even less than about 3.

Aqueous dispersions of nanodiamonds prepared according to the methods described herein may be further characterized by advantageous storage stability. For example, said aqueous dispersions may show no appreciable precipitation of the nanodiamond phase when stored for at least about 1 day, at least about 1 week, at least about 1 month, or at least about 4 months at ambient conditions.

Dry nanoparticulate compositions prepared according to the methods described herein are also within the scope of the present invention. Advantageously, dry nanodiamonds that have been disaggregated as described herein can be readily redispersed in water to form an aqueous dispersion having an only slightly larger mean particle size (e.g., a mean particle size of less than about 50 nm, less than about 40 nm, less than about 30 nm, less than about 25 nm, less than about 20 nm, or less than about 15 nm). This feature of the dry nanodiamond compositions is significantly advantageous compared to nanodiamonds prepared using prior art disaggregation techniques, where drying and subsequent redispersion resulted in the formation of aggregates having a mean particle size of 1 μm or greater.

While the text of this disclosure focuses on aggregated and disaggregated nanodiamonds, it should be appreciated that the same principles and considerations can be applied to disaggregate other hard materials.

Having described the invention in detail, it will be apparent that modifications and variations are possible without departing from the scope of the invention defined in the appended claims.

EXAMPLES

The following non-limiting examples are provided to further illustrate the present invention.

Example 1

Materials and Procedures

All nanodiamond powders used in these experiments were produced by detonation. Nanodiamond samples from three different manufacturers were designated ND1, ND2, and ND3, respectively, as listed in Table 1 below.

A portion of the nanodiamonds from each sample was purified in air at 425° C. for 2 hours in a ceramic crucible. The resulting purified samples each contained about 95-97 wt. % of nanodiamond terminated with carboxyl groups. These air-oxidized nanodiamond samples were labeled ND1-COOH, ND2-COOH, and ND3-COOH, respectively, in order to reflect their dominant surface chemistry (see Table 1).

TABLE 1

| Nanodiamond samples | |
|---|---|
| ND grade | Sample name |
| UD90 | ND1 |
| Air oxidized UD90 | ND1-COOH |
| Nanodiamond grey | ND2 |
| Air oxidized ND grey | ND2-COOH |
| Standard ND | ND3 |
| Air oxidized Standard ND | ND3-COOH |

In each of the methods described below, sodium chloride of reagent grade was purchased from Sigma-Aldrich and used as-received.

Salt-Assisted Ultrasonic Disaggregation (SAUD)

Test compositions were prepared using each of the nanodiamond samples listed in Table 1.

For each sample, a mixture of 10 grams of sodium chloride and 0.250 grams of nanodiamond powder was ground using a porcelain mortar and pestle and placed into a 20 mL glass scintillation vial along with 5 mL of DI water. The prepared composition was sonicated using a BRANSON SONIFIER™ 250 ULTRASONICATOR for 100 min at 60% output power and 50% duty cycle at 60 kHz frequency.

After sonication, the composition was equally split between two 50 mL plastic FALCON centrifuge tubes and dispersed in distilled water up to 100 mL total volume (2×50 mL). Each composition was then centrifuged using an EPPENDORF CENTRIFUGE 5810-R at 4000 rpm and 25° C. for 10 minutes and the clear supernatant was discarded. The wet nanodiamond precipitates were then redispersed in distilled water (100 mL total volume) and centrifuged a second time at 12000 rpm and 25° C. for 1 hour. Once again, the clear supernatant was discarded and the wet nanodiamond precipitates were redispersed in 5 mL of distilled water for characterization.

A standard AgNO₃ assay showed a complete absence of Cl⁻ in the disaggregated nanodiamonds. After evaporation of water from the samples, formation of black solid nanodiamond "chips" was observed with a yield of ~200 mg, for an 80% yield relative to the initial nanodiamond mass of each sample.

Example 2

Fourier Transform Infrared Spectroscopy

To demonstrate that salt-assisted ultrasonic disaggregation works with different nanodiamond grades from different sources, nanodiamonds from samples ND2 and ND3, as well as nanodiamonds from the air-oxidized ND2-COOH and ND3-COOH samples, were studied using Fourier Transform Infrared (FTIR) spectroscopy.

The FTIR spectra were recorded in the 800-4000 cm$^{-1}$ range at 1 cm$^{-1}$ resolution using a THERMO NICOLET NEXUS 470 FTIR spectrometer. The FTIR spectra of nanodiamonds were recorded in potassium bromide pellets made by pressing the mixture of 100 mg KBr and 1 mg ND under a load of 15 tons.

It was observed that salt-assisted ultrasonic disaggregation of either ND2 or ND3 nanodiamonds did not produce single-digit nanodiamond particles. However, salt-assisted ultrasonic disaggregation of both ND2-COOH and ND3-COOH was observed to yield stable single-digit nanodiamonds.

Figure 2A:
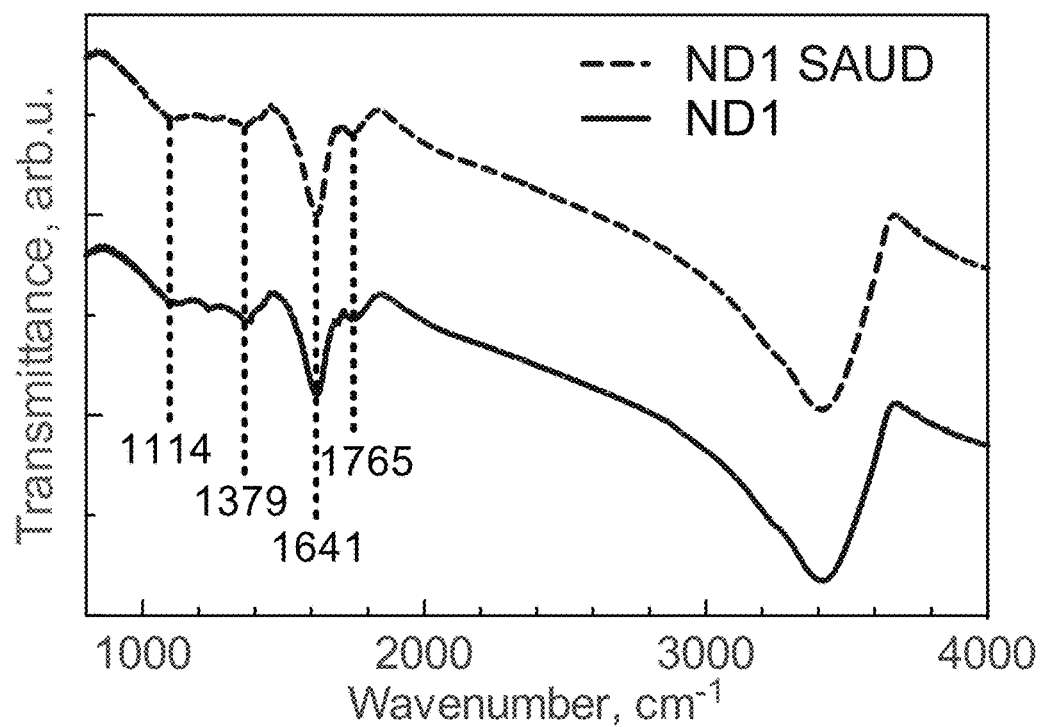
FIGS. 2A, 2B, 2C, and 2D depict the FTIR data discussed in Example 2.
Figure 2B:
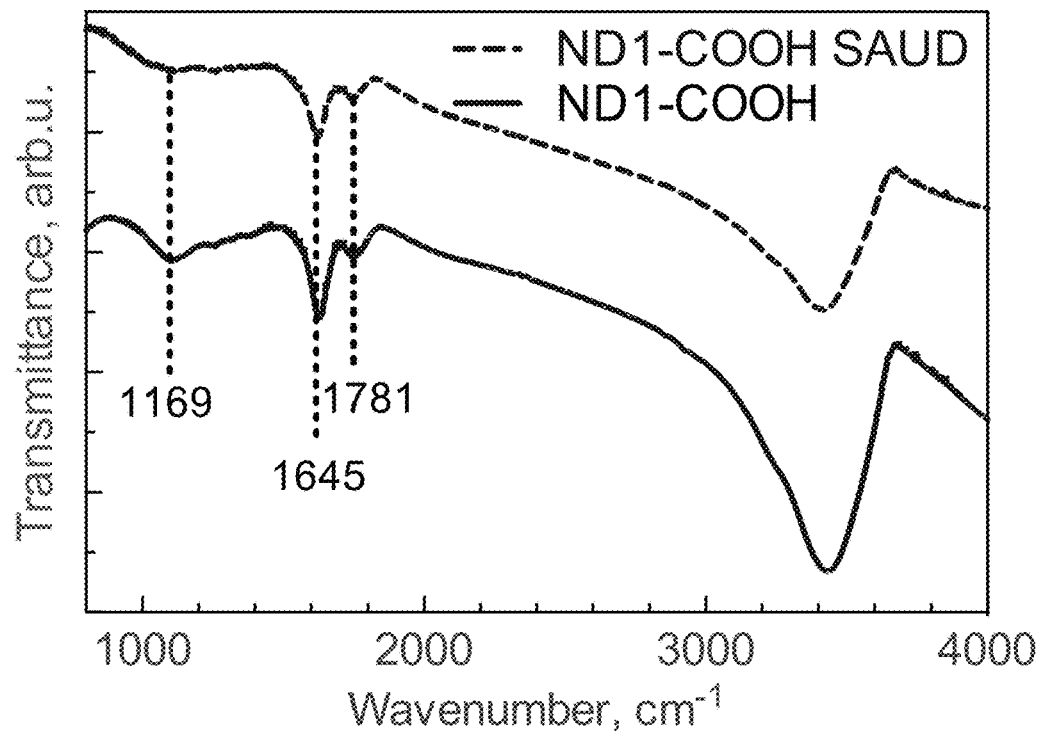
Figure 2C:
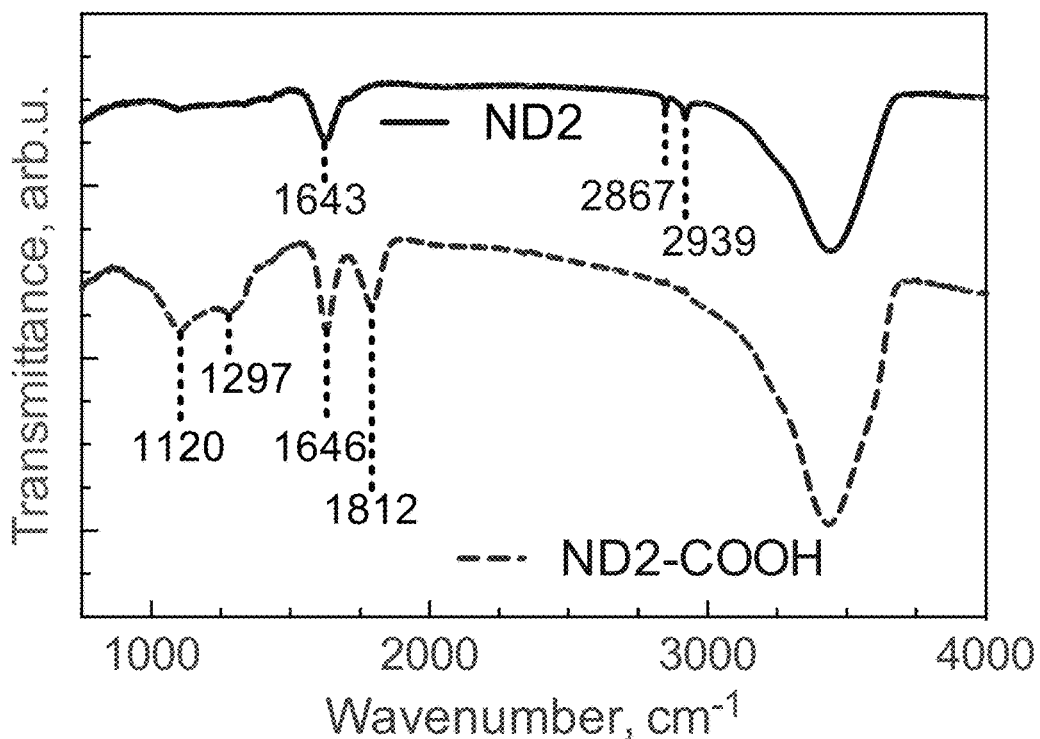
Figure 2D:
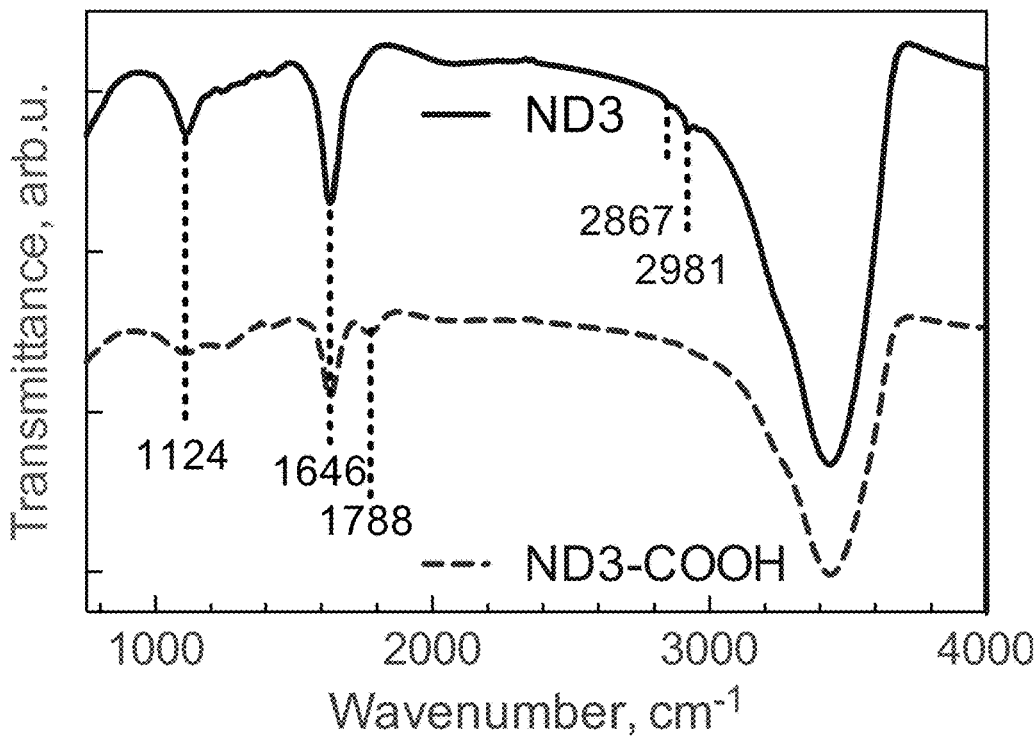

As shown in FIGS. 2c and 2d, FTIR indicates dramatic differences in surface chemistry between ND2 and ND2-COOH as well as between ND3 and ND3-COOH. The FTIR spectrum of ND2 and ND3 reveals a complete absence of the C=O stretch (appearing at 1812 and 1788 cm$^{-1}$ in the corresponding spectra of the oxidized NDs) and presence of the C—H stretch vibration peaks (2867, 2939 for ND2 and 2867, 2981 cm$^{-1}$ for ND3). This indicates the absence of COOH groups on ND2 and ND3, higher content of CH$_2$/CH$_3$ groups, and the presence of OH, either chemically attached to ND surface or in adsorbed water.

These results suggest that salt-assisted ultrasonic disaggregation works better with hydrophilic nanodiamonds that have a large number of carboxyl groups on the surface. Fortunately, virtually any nanodiamond sample can be made amenable to salt-assisted ultrasonic disaggregation after a simple air oxidation step, which removes non-diamond carbon and forms COOH groups on the surface.

As shown in FIGS. 2a and 2b, there were no observed changes in FTIR spectra of the disaggregated ND1 and ND1-COOH nanodiamonds as compared to the initial nanodiamond clusters. Accordingly, under the experimental conditions described above, it was observed that salt-assisted ultrasonic disaggregation did not alter the nanodiamond surface chemistry.

Example 3

Process Kinetics and Particle Size Distribution

Kinetics of the salt-assisted ultrasonic disaggregation process described in Example 1 were explored by taking 1 mL aliquots from the test composition at intervals of 30, 60, and 100 min into the sonication process. The aliquots were subjected to two consecutive water washing and centrifugation steps to remove NaCl, followed by dilution to ~0.2 wt. % nanodiamond before measuring the particle size distribution.

Dynamic Light Scattering (DLS) measurements obtained using a ZETASIZER NANO ZS were used to determine the particle size distribution of the nanodiamond dispersions. The same instrument was employed to measure zeta-potential of nanodiamonds using electrophoretic mobility. The measured particle size distributions were found to be sensitive to solution viscosity, which in turn depends on the nanodiamond concentration. Each measurement was taken in triplicate, and the mean values are plotted in FIGS. 1 and 3. A MPT-2 auto-titrator was used to measure particle size and zeta-potential versus pH.

The particle size distribution of an aqueous suspension of neat ND1 nanodiamonds, measured by DLS, typically shows two broad peaks centered at 800 and 150 nm (FIG. 1a, 0 min), which correspond, respectively, to "intermediate" and "core" nanodiamond aggregates. Suspension of neat ND1-COOH showed a smaller average particle size, with a single peak centered at 70-80 nm (FIG. 1b, 0 min). This observation is consistent with previously reported data that due to the high content of surface carboxyl groups, air purified nanodiamonds have a more uniform and hydrophilic surface than as-received nanodiamonds.

Figure 1B:
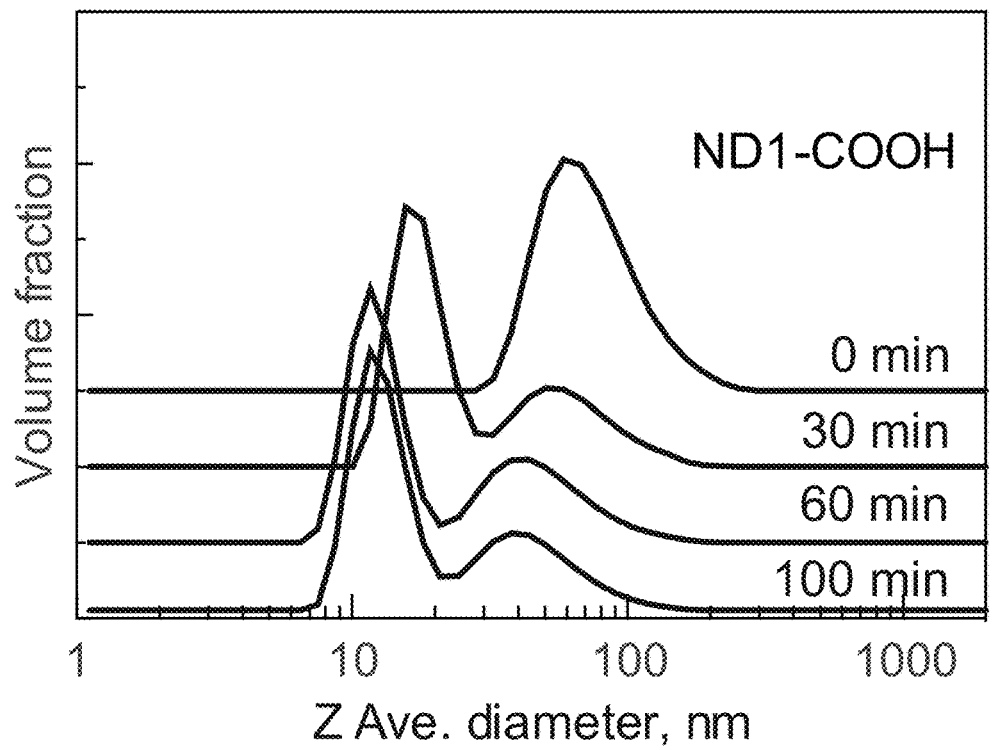

During the salt-assisted ultrasonic disaggregation of sample ND1, FIG. 1a shows that after 30 min a peak at ~800 nm disappeared and a peak at ~150 nm reduced in intensity and shifted towards smaller size at 70 nm. Within the same period of time, a new intense and narrow peak at 21-25 nm appeared, corresponding to small nanodiamond aggregates of only a few particles each. After 60 min of salt-assisted ultrasonic disaggregation, the peaks further moved towards smaller sizes as compared to 30 min. A significant reduction in size was observed after 100 min of salt-assisted ultrasonic disaggregation with an intense peak at 13 nm followed by a tail peaked at ~40 nm. Notably, salt-assisted ultrasonic disaggregation was difficult to continue beyond 100 min, due to the dramatically increased viscosity of the slurry reducing the efficiency of ultrasound propagation.

A kinetics study for ND1-COOH was performed similarly, and the results are shown in FIG. 1b. The same trends were observed, although after 100 min of SAUD the size of ND1-COOH was even smaller: the particle size distribution showed an intense peak at 11 nm followed by a tail at 30 nm. Without being bound to a particular theory, it is believed that due to a greater hydrophilicity of the air-oxidized ND1-COOH, this nanodiamond sample demonstrated a better particle size distribution following the same salt-assisted ultrasonic disaggregation process as compared to the ND1 nanodiamond sample.

It is well known that viscosity plays a significant role in DLS, and that the particle size for a nanodiamond suspension is dependent on the concentration and therefore the viscosity of a given sample. DLS studies of aqueous nanodiamond suspensions in the concentration range of 0.01-5 wt % have been determined to have viscosities in the range of 0.9-1.8 mPa with a particle size range of 30-5 nanometers, respectively. The behavior of concentrated nanodiamond suspensions may be explained by the formation of colloidal crystals where nanodiamond particles are uniformly distributed with 10 nanometers of distance between each crystal, resulting in a much greater sample viscosity. Diluted samples, however, exhibit an increase in interparticle distance, therefore forming a more preferential environment for the formation of nanodiamond secondary aggregates and an increased aggregate size.

Particle size distribution for 4 wt % nanodiamond suspensions in water was determined to be different than for the 0.2 wt % nanodiamond suspensions discussed above.

Adjusting the viscosity setting to 2.0-2.3 cP for DLS measurements for the 4 wt % nanodiamond suspensions revealed a particle size distribution having a peak at 6-8 nanometers with a small tail at 20-30 nanometers simultaneously for ND1, ND1-COOH, and ND2-COOH. The suspensions each appeared to be very stable, having no precipitation at ambient conditions for over 1 month.

Example 4

Zeta Potential and Isoelectric Point

Observations of Zeta potential versus pH for nanodiamond samples before and after salt-assisted ultrasonic disaggregation provide additional evidence for the formation of single-digit nanodiamond suspensions.

The initial zeta potential of nanodiamond was of negative charge at neutral pHs due to surface groups such as carboxylic functions and graphitic shells. However, each treated (disaggregated) sample appeared to show a more negative zeta potential when compared to non-treated (aggregated) nanodiamond samples. Without being bound to a particular theory, this may be due to the fact that in disaggregated samples, the surface groups become more exposed as compared to aggregated samples.

FIG. 4 shows Zeta potential versus pH in dashed lines and Z average diameter versus pH in solid lines. The circle data points represent nanodiamonds (NDs) before salt-assisted disaggregation (SAUD) and the square data points represent NDs after SAUD. FIG. 4a shows these data for ND1 (circles) and ND1 after SAUD (squares). FIG. 4b shows these data for ND1-COOH (circles) and ND1-COOH after SAUD (squares). FIG. 4c shows these data for ND2-COOH (circles) and ND2-COOH after SAUD (squares). FIG. 4d shows these data for ND3-COOH (circles) and ND3-COOH after SAUD (squares). With respect to the Zeta potential data, the isoelectric point (IEP) determination for ND1 and ND1-COOH samples was found to be 2.8-2.9, while the corresponding disaggregated samples following SAUD treatment had an IEP of around 2.0 each. In the case of ND2-COOH, it was observed that pH 2 was not acidic enough to reach the isoelectric point. After SAUD treatment, disaggregated ND2-COOH samples had an 11 mV lower zeta potential as compared to the non-treated starting material (FIG. 4c).

Example 5

Analysis of pH and Particle Size

Figure 4A:
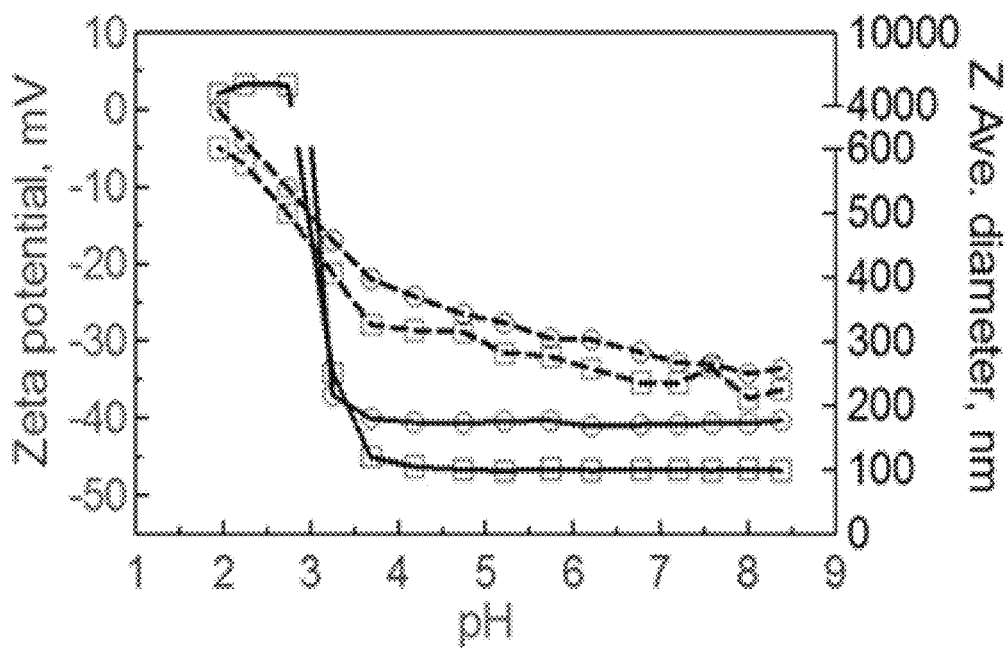
FIGS. 4A, 4B, 4C, and 4D depict the Zeta potential of nanodiamond compositions discussed in Example 4.
Figure 4B:
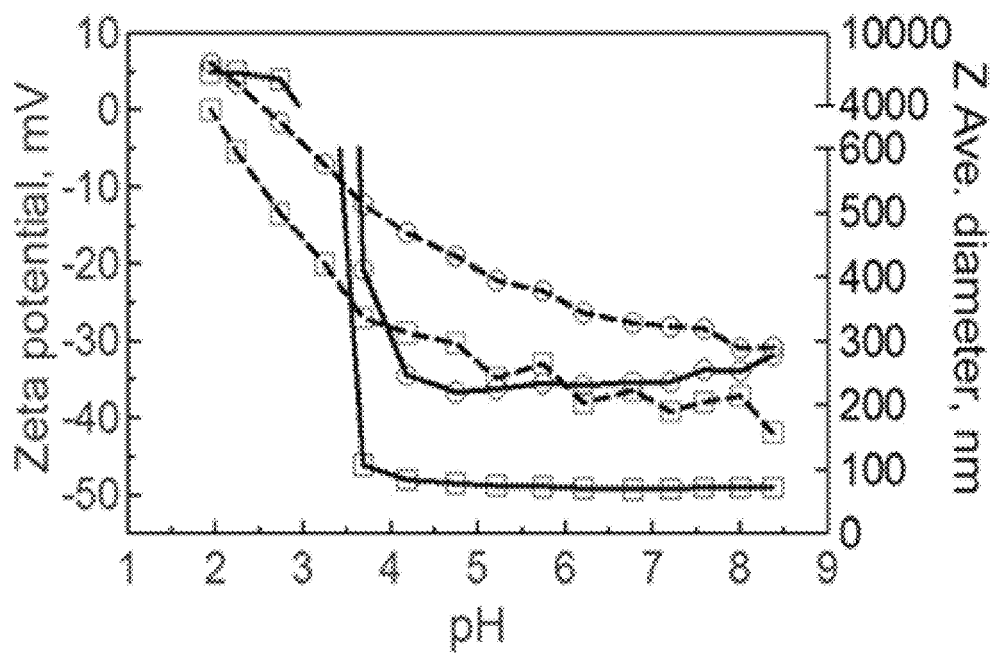
Figure 4C:
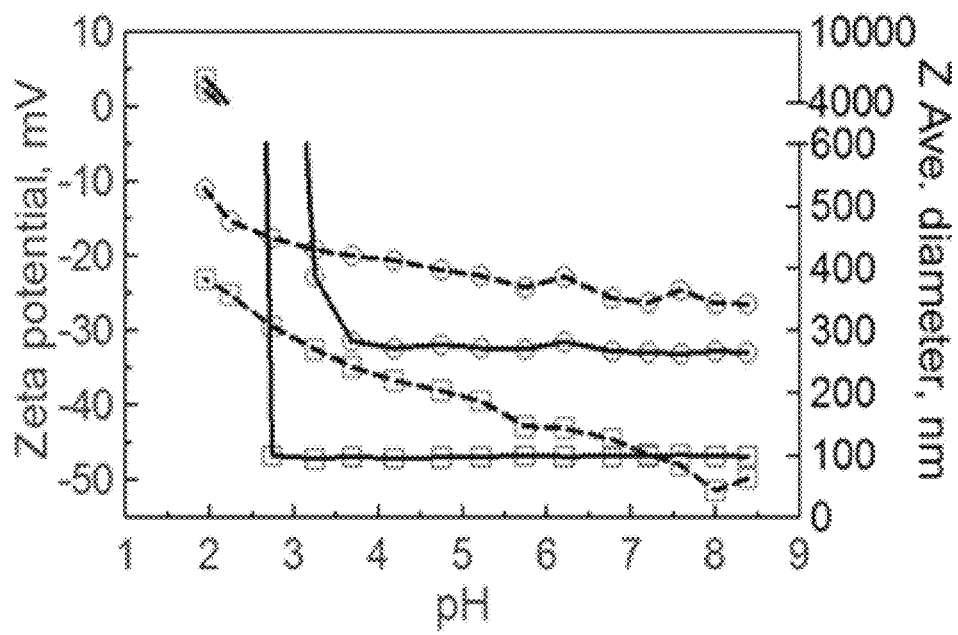
Figure 4D:
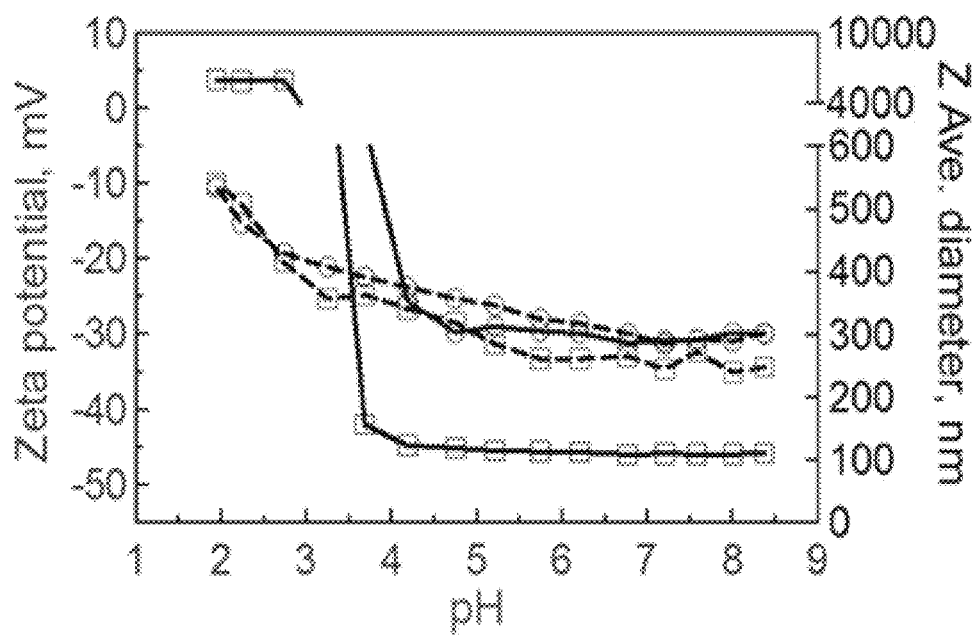

In terms of aggregation behavior, SAUD results in a better colloidal stability of NDs down to lower pH values. Size versus pH studies are illustrated with the solid lines in FIG. 4. FIG. 4a shows that for ND1 both before and after SAUD, aggregation begins when the pH drops to below about 3.2. FIGS. 4b and 4d show that for ND1-COOH and ND3-COOH, with SAUD treatment aggregation begins at a pH lower than 4.0; but at a pH higher than 4.0 without SAUD treatment. FIG. 4c shows that for ND2-COOH, with SAUD treatment there is extreme stability down to pH 2.7; as compared to moderate down to only 3.3 or even higher without SAUD treatment. The differences between untreated and SAUD-treated NDs demonstrate an improvement in colloidal behavior of both greater stability and greater pH range of stability with SAUD treatment. The differences in colloidal behavior observed between different SAUD-treated NDs underscore the role of surface chemistry, in particular the number of COOH groups in these samples. NDs with high colloidal stability in a broader pH range produced by SAUD (e.g., ND2-COOH SAUD) are of particular interest for biomedical applications, in which stability at lower pH is often required.

For SAUD-treated ND1, the aggregation point started much higher at pH of 3.5. Without being bound to a particular theory, this significant difference in nanodiamond behaviors supports the impact of surface chemistry on the salt-assisted ultrasonic disaggregation process.

Example 6

Optical Measurements and Color Observations

UV-Vis spectra of the disaggregated colloidal nanodiamond solutions prepared as described in Example 1 above were acquired using a VARIAN CARY 50 BIO UV-visible spectrophotometer.

Absorbance spectra in the range of 400-800 nm were recorded for SAUD-treated (disaggregated) ND1, ND1-COOH, ND2-COOH, and ND3-COOH colloidal compositions. Absorbance at 400 nm versus mass concentration of nanodiamond was plotted and the weight extinction coefficients were derived from the calculated linear regression slopes. The Tyndall effect confirms colloidal state of SAUD-treated nanodiamonds in aqueous compositions.

SAUD treatment also resulted in dramatic changes in the color of nanodiamond suspensions observed for all nanodiamond samples studied. (FIG. 3, lower inset photos are darker than the upper inset photos).

It is known that well-dispersed nanodiamonds in water have a darker color compared to aggregated samples. The single-digit aqueous nanodiamonds have characteristic, almost black appearance. The origin of the dark color of aqueous nanodiamond colloids is still debated, however, by adjusting the pH it has been proven in literature that the change in color during deaggregation is not related to light absorbance by graphitic carbon impurities. Many factors, including light scattering, absorbance by surface states, contribute to the color of single-digit nanodiamond colloids in addition to bulk absorbance. However, even without detailed knowledge of light interaction with nanodiamonds, the changes in color can be used to make qualitative conclusions about particle size in nanodiamond dispersions.

Figure 3A:
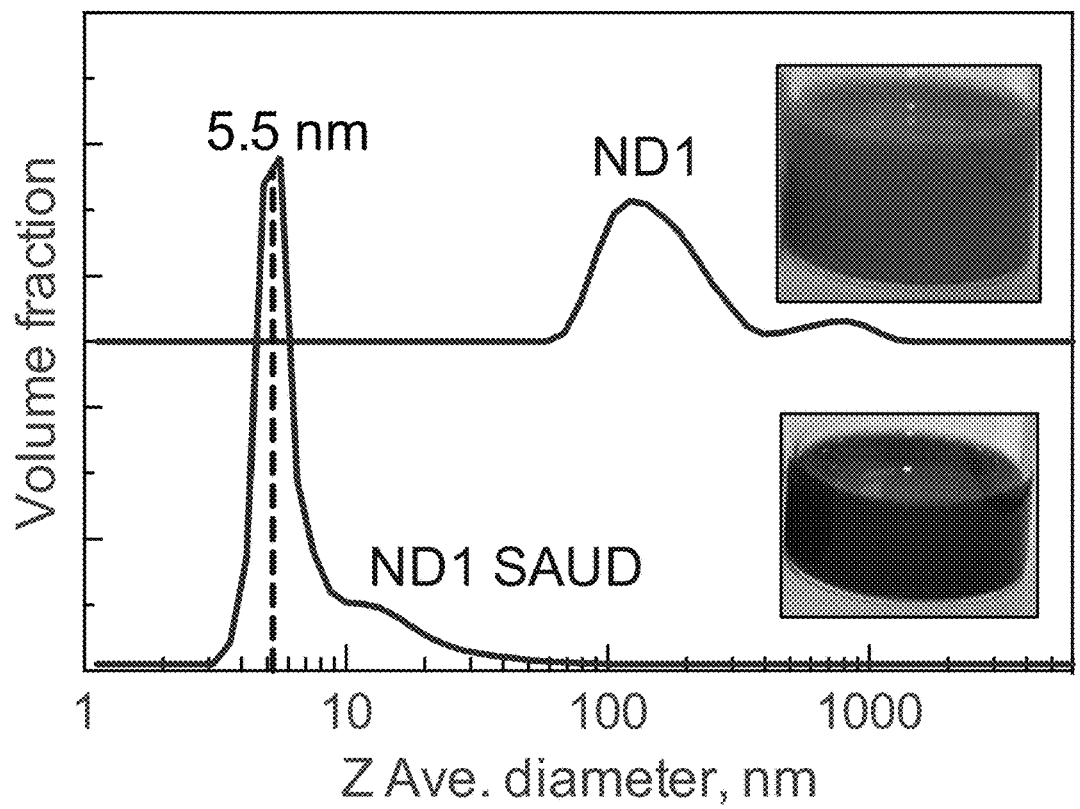
FIGS. 3A, 3B, 3C, and 3D depict the particle size distribution and photographs of initial and disaggregated nanodiamond compositions discussed in Example 6.
Figure 3B:
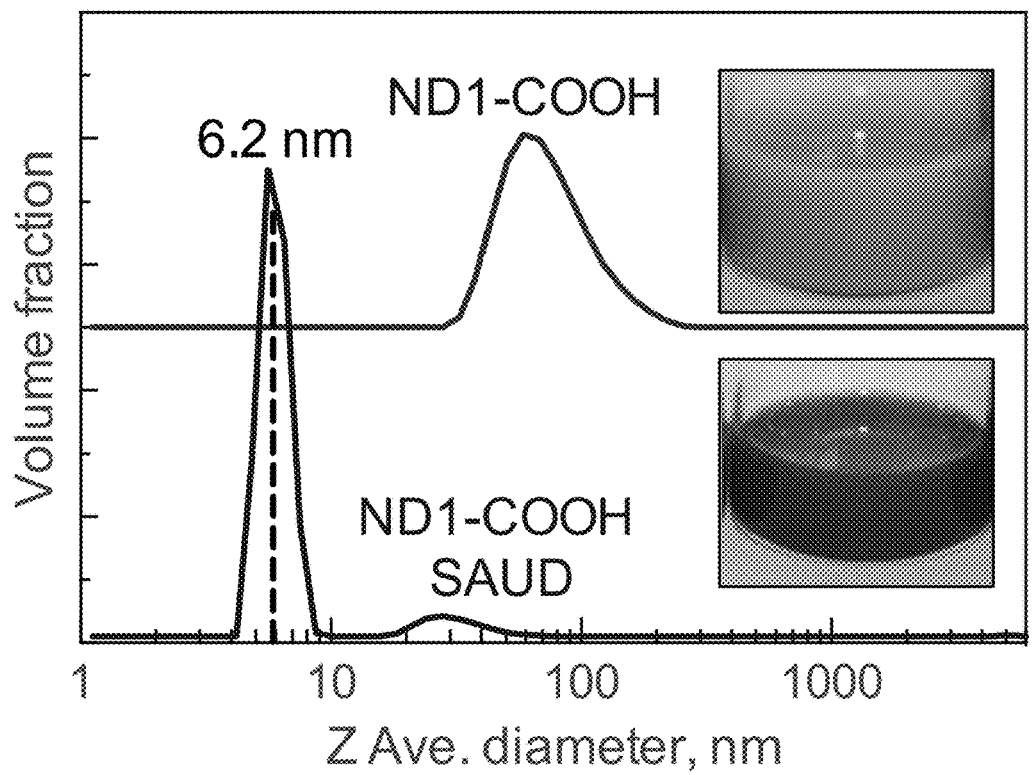
Figure 3C:
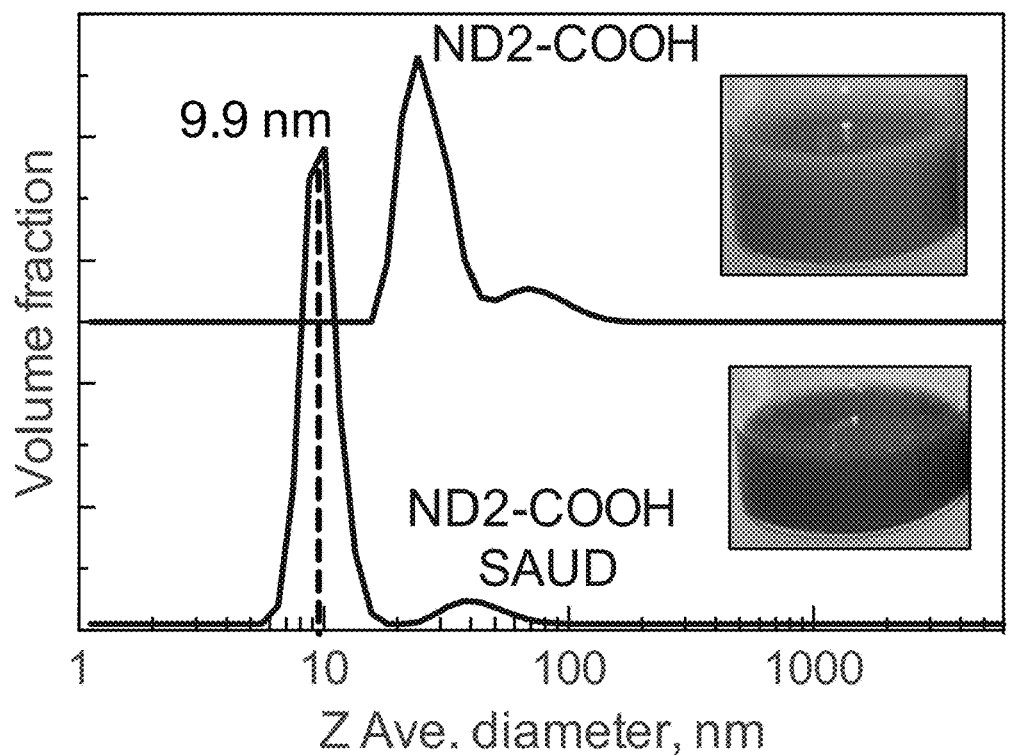
Figure 3D:
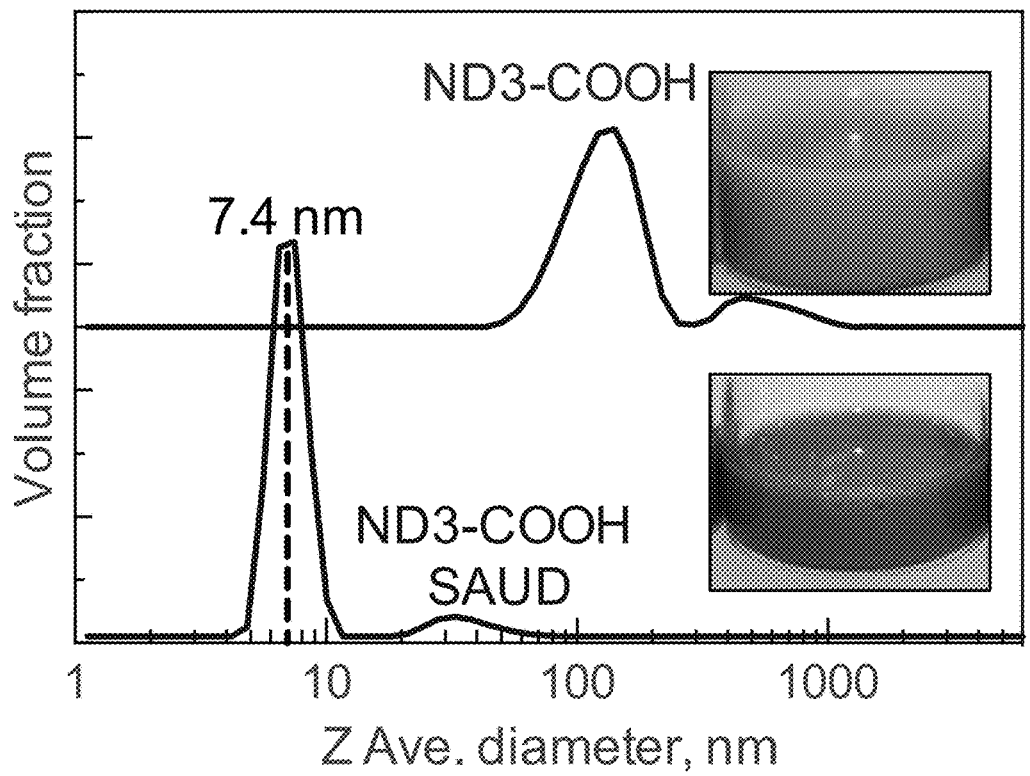

ND1 has a brownish color in suspension (FIG. 3a, upper inset), while the color of SAUD ND1 is intensely black-brownish at same concentration (FIG. 3a, lower inset). ND1-COOH, ND2-COOH and ND3-COOH appear to be grey or light grey (FIG. 3, upper insets), whereas the SAUD-treated samples all become black-brownish (FIG. 3, lower insets), a sign of single-digit nanodiamonds.

Light absorbance can be used for determination of nanodiamond concentration. To this end, it is important to know nanodiamond extinction coefficients. We have used different concentrations of SAUD-treated nanodiamonds to determine their mass extinction coefficients at 400 nm. The calculated mass extinction coefficients are 1.880, 0.841, 0.999, and 1.206 mg·mL$^{-1}$·cm$^{-1}$ for SAUD-treated ND1, ND1-COOH, ND2-COOH, and ND3-COOH, respectively.

Example 7

Transmission Electron Microscopy (TEM) and Energy-Dispersive X-Ray (EDX) Spectroscopy TEM was carried out with a PHILIPS TECNAI F30 field-emission electron microscope operated at 200 kV. TEM samples were prepared by drop casting ND aqueous colloidal solutions onto carbon-coated Cu grids followed by drying in ambient air atmosphere. EDX was performed in TEM with 130 eV energy resolution using Li-drift Si detector. Additional structural information was obtained by Small Area Electron Diffraction (SAED), also performed in TEM.

Figure 5A:
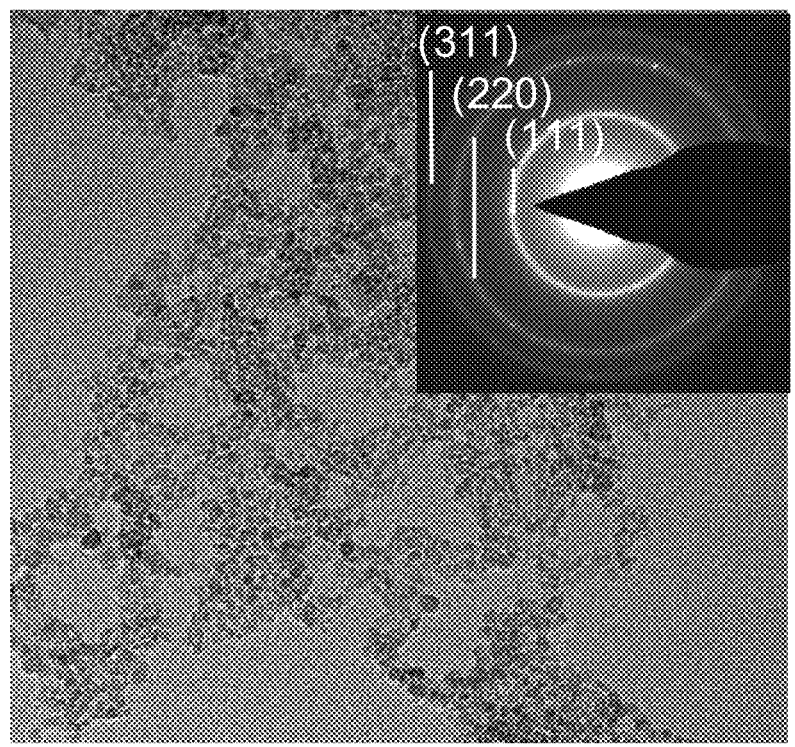
FIGS. 5A, 5B, 5C, and 5D depict a TEM image of nanodiamond compositions discussed in Example 7.
Figure 5B:
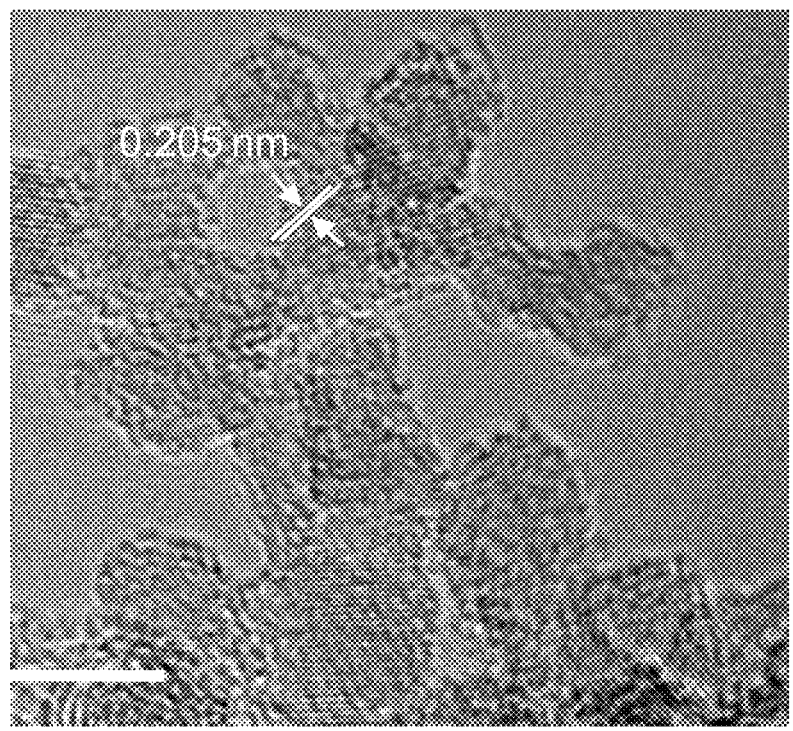

Additional characterization of SAUD-treated nanodiamonds was performed by transmission electron microscopy (TEM) and X-ray diffraction (XRD). FIG. 5a shows representative TEM images of SAUD-treated ND1 drop-casted on the carbon coated copper grid from a colloidal solution. No dense dark aggregates of nanodiamonds can be seen in a wide-field low-resolution image. The sample appears uniform and the nanodiamonds form a loose monolayer. The inset of FIG. 5a is a selected-area electron diffraction (SAED), which confirms that the SAUD-treated nanodiamond particles retain their diamond crystalline structure. The SAUD rings correspond to (111), (220) and to (311) planes of nanodiamond with d spacing 0.204 (also confirmed by HR-TEM shown in FIG. 5b), 0.126, and 0.108 nm, respectively. The measured d spacing values match well with a structure of cubic diamond.

Figure 5C:
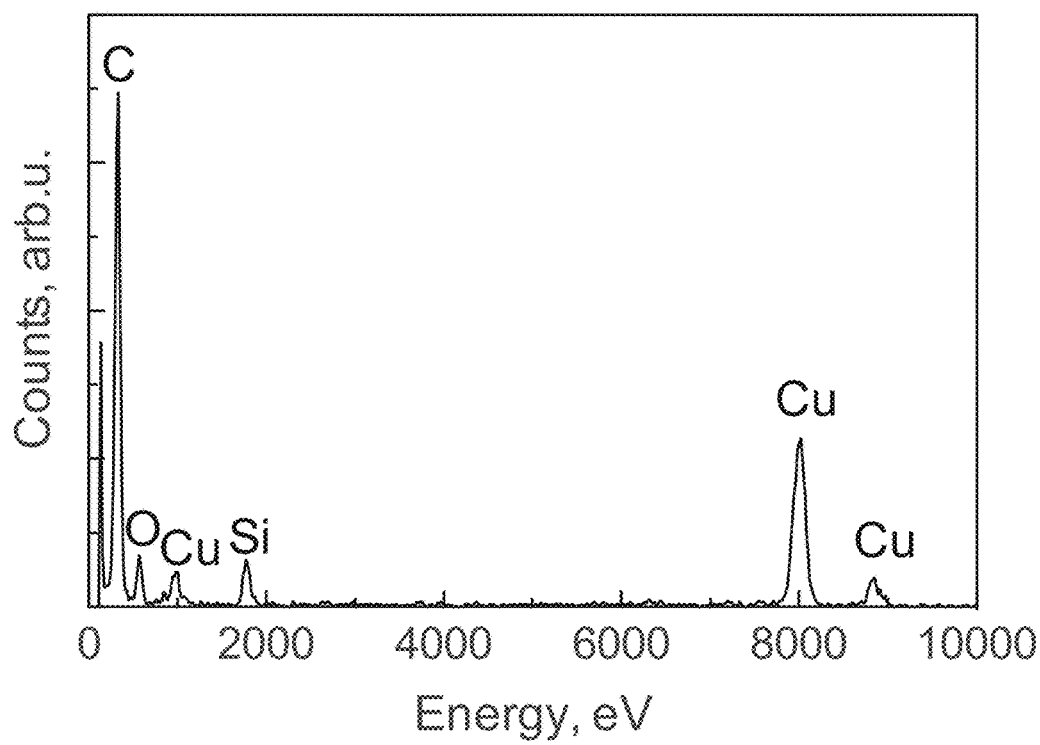

The chemical composition of the particles was assessed by energy-dispersive spectroscopy (EDX). As expected, the EDX (FIG. 5c) of the SAUD-treated ND1 shows mainly carbon, indicating high purity of the samples. The signals of other elements observed in the EDX spectrum are coming from the TEM grid (Cu) and TEM detector (Si).

Figure 5D:
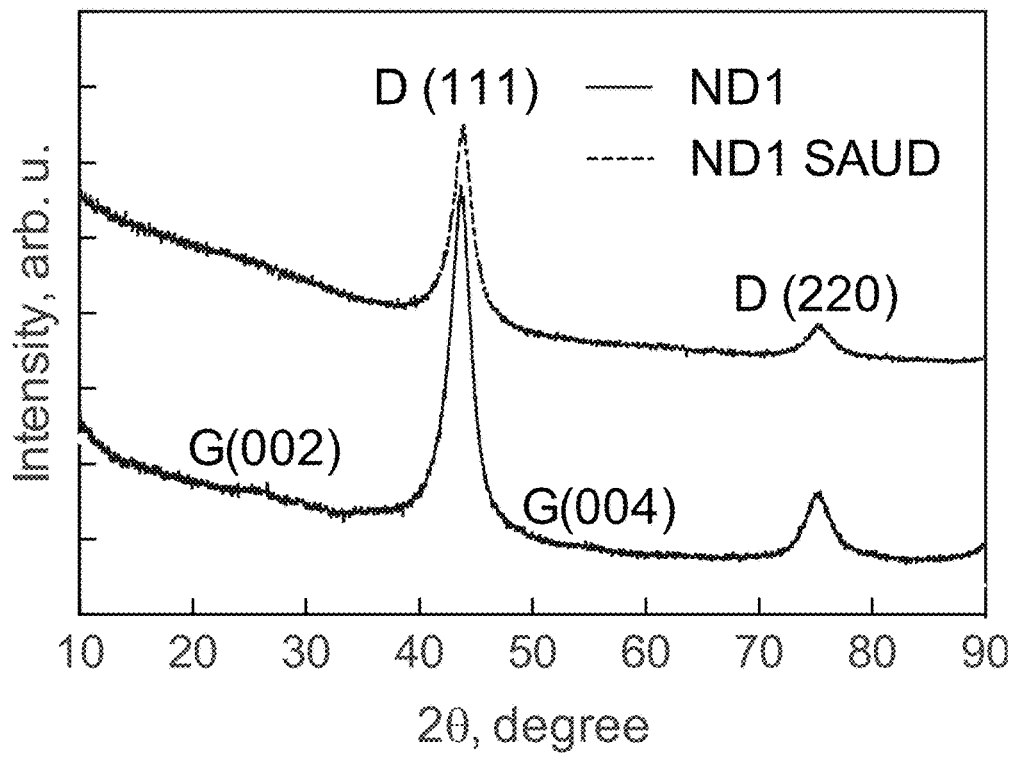

In contrast to XRD pattern of the initial aggregated ND1 (lower line in FIG. 5d), the XRD pattern of SAUD-treated ND1 (upper line in FIG. 5d) does not show any intensity in the positions (002) and (004) peaks related to graphite shells. Well pronounced peaks at 2θ=43.9° and 75.3°, which correspond to diamond core, are in a good agreement with previously reported diffraction data (PDF Card 00-006-0675). According to Scherer's equation, the crystal size of SAUD-treated ND1 was calculated to be 4.4 nm, which is slightly less than in non-treated (aggregated) ND1 (4.6 nm). Both EDX and XRD analyses confirm that in contrast to other nanodiamond de-aggregation techniques, no contaminations (like $ZrO_2$, $SiO_2$, iron oxides, etc.) are introduced by SAUD.

Example 8

Additional Disaggregating Agents

Salt assisted ultrasonic disaggregation of ND1 nanodiamond aggregates was carried out as described in Example 1, but using disaggregating agents other than sodium chloride.

Figure 6A:
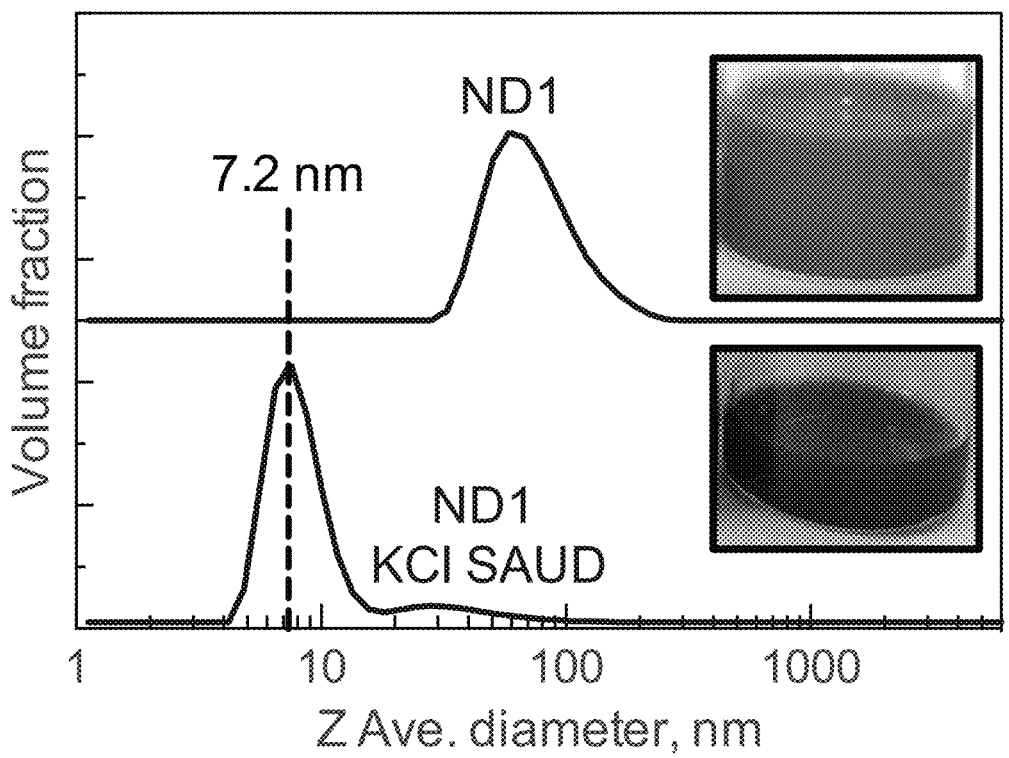
FIGS. 6A and 6B depict the particle size distribution of nanodiamond aqueous dispersions discussed in Example 8.
Figure 6B:
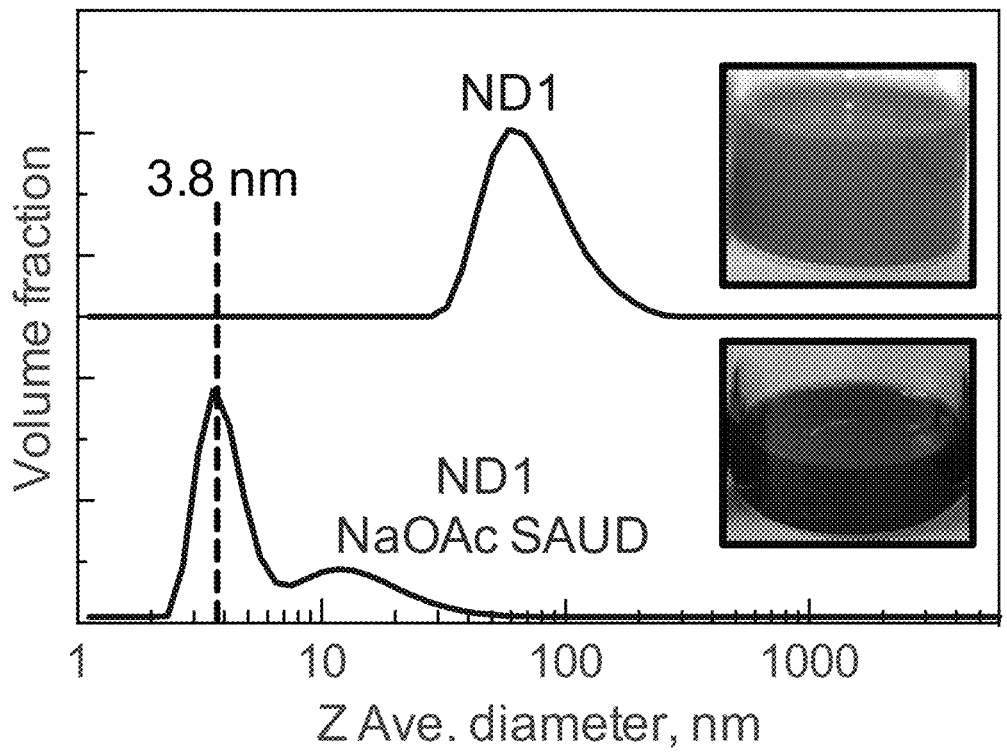

By following the SAUD protocol described in Example 1 (using a mass ratio of water to disaggregating agent to nanodiamond of 100:200:5), but replacing the NaCl with potassium chloride, disaggregated nanodiamond particles having an average particle size of 7.2 nm were achieved (FIG. 6a). Using an identical protocol, but with sodium acetate as the disaggregating agent, resulted in disaggregated nanodiamond particles having an average particle size of 3.8 nm in water (FIG. 6b). In both experiments, the particle size distributions were measured at 4 wt. % nanodiamond concentration in a colloidal solution and at a viscosity of 1.6 mPa·s.

Example 9

X-Ray Photoelectron Spectroscopy

Chemical composition data in below Tables 2-3 show that the content of the alkali metal is within 0.72-0.85 at %., while chlorine content is negligible (~0.06at %), supporting the hypothesis about formation of the ND salts of respective alkali metals during NaCl and KCl SAUD. Moreover, the formation of ND-COO$^-$Na$^+$ (ND-COO$^-$K$^+$) is expected in these circumstances based on simple chemical considerations, assuming that ND-COOH is a weak acid (weaker than HCl), which seems to be a valid assumption.

Salt assisted ultrasonic disaggregation of ND1 nanodiamond aggregates was carried out as described in Example 1 (using sodium chloride as the disaggregating agent) and Example 8 (using potassium chloride as the disaggregating agent.) Characterization of the resulting SAUD-treated nanodiamonds was performed using X-ray photoelectron spectroscopy (XPS).

The data in Table 2 demonstrate that for the SAUD-treated nanodiamonds processed using sodium chloride, the content of the alkali metal in the liquid medium is within a range of from about 0.72 to about 0.85 atomic percent, while chlorine content is negligible (~0.06 at. %). Similar results were observed or the SAUD-treated nanodiamonds processed using potassium chloride, as shown in Table 3. The XPS quantification report of SAUD-treated nanodiamonds processed with sodium chloride is presented in Table 2 below; the corresponding data for SAUD-treated nanodiamonds processed with potassium chloride are presented in Table 3 below.

TABLE 2

XPS quantification report of SAUD ND1 processed with sodium chloride.

| Peak | Atomic Conc. % |
| --- | --- |
| Na 1s | 0.82 |
| Fe 2p | 0.21 |
| O 1s | 11.35 |
| Ti 2p | 0.21 |
| N 1s | 2.13 |
| C 1s | 84.66 |
| Cl 2p | 0.06 |
| Si 2p | 0.57 |

TABLE 3

XPS quantification report of SAUD ND1 processed with potassium chloride.

| Peak | Atomic Conc. % |
| --- | --- |
| Fe 2p | 0.26 |
| O 1s | 9.61 |
| N 1s | 2.07 |
| K 2s | 0.75 |
| C 1s | 86.80 |
| Cl 2p | 0.06 |
| Si 2p | 0.45 |

These data indicate the formation of nanodiamond salts of the respective alkali metals (e.g., sodium and potassium, respectively). Without being bound to a particular theory, the formation of ND—COO$^-$Na$^+$ and ND-COO$^-$K$^+$ would be expected in these circumstances based on simple chemical considerations, assuming that ND-COOH is a weak acid (weaker than HCl), which appears to be a valid assumption.

When introducing elements of the present invention or the embodiments(s) thereof, the articles "a", "an", "the" and "said" are intended to mean that there are one or more of the elements. The terms "comprising", "including" and "having" are intended to mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawing[s] shall be interpreted as illustrative and not in a limiting sense.

What is claimed is:

1. A method of disaggregating nanodiamond clusters, the method comprising:
   (a) combining aggregated nanodiamond clusters with a disaggregating agent in a liquid medium comprising a solvent, with the disaggregating agent being present in a concentration above its solubility limit in the solvent to form a mixture of solvent, disaggregating agent, and nanodiamond clusters; and
   (b) sonicating the mixture for a time sufficient to produce nanodiamond particles having a median particle size less than the median particle size of the aggregated nanodiamond clusters,
   wherein a mass ratio of disaggregating agent to nanodiamond particles in the liquid medium is from about 10:1 to about 100:1.

2. The method of claim 1 wherein the disaggregating agent comprises a crystalline inorganic salt.

3. The method of claim 2 wherein the disaggregating agent comprises a halide salt.

4. The method of claim 2 wherein the disaggregating agent comprises a chloride salt.

5. The method of claim 4 wherein the disaggregating agent comprises sodium chloride.

6. The method of claim 1 wherein the disaggregating agent comprises a crystalline sugar, organic acid, or organic salt.

7. The method of claim 1 wherein the disaggregating agent comprises a chloride, sulfate, or nitrate of gadolinium, copper, nickel, iron, or cobalt.

8. The method of claim 1 wherein the disaggregating agent comprises sodium chloride.

9. The method of claim 8 wherein the solvent comprises a non-aqueous organic solvent.

10. The method of claim 9 wherein the disaggregating agent is at least partially soluble in the solvent component, and wherein the liquid medium comprises the disaggregating agent in an amount that exceeds its solubility limit in the solvent component.

11. The method of claim 10 wherein the liquid medium comprises the disaggregating agent in an amount of greater than 200% of its solubility limit in the solvent component.

12. The method of claim 1 wherein the mass ratio of the disaggregating agent to the nanodiamond in the liquid medium is at least about 150:1.

13. The method of claim 1 wherein the liquid medium is sonicated for a period of from about 30 minutes to about 120 minutes.

14. The method of claim 1 further comprising a separation step wherein at least a portion of the disaggregating agent is separated from the nanodiamond particles by dissolving at least a portion of the disaggregating agent in an eluting solvent in which the nanodiamond particles are substantially insoluble and in which the disaggregating agent is soluble.

15. The method of claim 14 wherein the eluting solvent comprises water.

16. The method of claim 1 comprising an air oxidation step prior to the disaggregation step, wherein said air oxidation step comprises heating the aggregated nanodiamond clusters in air at a temperature of at least about 350° C. for a period of at least about 5 minutes.

17. The method of claim 1 wherein the method is performed in the absence of ceramic or metallic milling media.

18. The method of claim 1 wherein:
   the mixture of solvent, disaggregating agent, and nanodiamond clusters comprises sodium chloride as the disaggregating agent and water as the solvent;
   the sodium chloride is present in a concentration greater than 200% of its solubility limit in the water;
   the disaggregating agent is present in a mass ratio to the nanodiamond clusters of at least about 150:1;
   the nanodiamond clusters are present in a concentration of at least about 30 g/L; and
   the sonication is for between about 5 minutes to about 120 minutes.

19. The method of claim 1 comprising an ozone oxidation step prior to the disaggregation step.

20. The method of claim 1 wherein:
   the mixture of solvent, disaggregating agent, and nanodiamond clusters comprises sodium chloride as the disaggregating agent and water as the solvent;
   the sodium chloride is present in a concentration greater than 200% of its solubility limit in the water;
   the disaggregating agent is present in a mass ratio to the nanodiamond clusters of at least about 20:1;
   the nanodiamond clusters are present in a concentration of at least about 30 g/L; and
   the sonication is for between about 30 minutes to about 120 minutes.

21. The method of claim 1 wherein:
   the mixture of solvent, disaggregating agent, and nanodiamond clusters comprises sodium chloride as the disaggregating agent and water as the solvent;
   the sodium chloride is present in a concentration greater than 200% of its solubility limit in the water;
   the disaggregating agent is present in a mass ratio to the nanodiamond clusters of from about 25:1 to about 75:1;
   the nanodiamond clusters are present in a concentration of at least about 30 g/L; and
   the sonication is for between about 30 minutes to about 120 minutes.

* * * * *